United States Patent [19]

Palmer et al.

[11] Patent Number: 5,025,806
[45] Date of Patent: Jun. 25, 1991

[54] MEDICAL VENTILATING AND A SPIRATING APPARATUS AND METHODS

[75] Inventors: Darrel Palmer, Sandy, Utah; Richard Radford, Auburn, Wash.

[73] Assignee: Ballard Medical Products, Midvale, Utah

[21] Appl. No.: 509,665

[22] Filed: Apr. 16, 1990

[51] Int. Cl.[5] .............................................. A61M 16/00

[52] U.S. Cl. .......................... 128/203.12; 128/203.15; 128/207.14

[58] Field of Search ...................... 128/207.14, 207.16, 128/203.15, 203.23, 203.12; 604/99, 174, 175

[56] References Cited

U.S. PATENT DOCUMENTS

| | | | |
|---|---|---|---|
| 3,831,629 | 8/1974 | Mackal et al. | 604/99 X |
| 4,240,417 | 12/1980 | Holever | 128/203.12 |
| 4,454,887 | 6/1984 | Krüger | 128/772 |
| 4,569,344 | 2/1986 | Palmer | 128/207.16 |

OTHER PUBLICATIONS

Respiratory Case, Nov. 1989, vol. 34, No. 11.
Marquest Literature—undated.
Instrument industries Literature—undated.

*Primary Examiner*—Clifford D. Crowder
*Assistant Examiner*—E. P. Raciti
*Attorney, Agent, or Firm*—Lynn G. Foster

[57] ABSTRACT

Ventilating/aspirating apparatus, and related methods, the apparatus comprising novel medication effluent structure forming a part of a ventilating/aspirating fitting immediately adjacent the patient by which a metered predetermined dosage of respirating medication is introduced as an atomized spray using one hand.

12 Claims, 3 Drawing Sheets

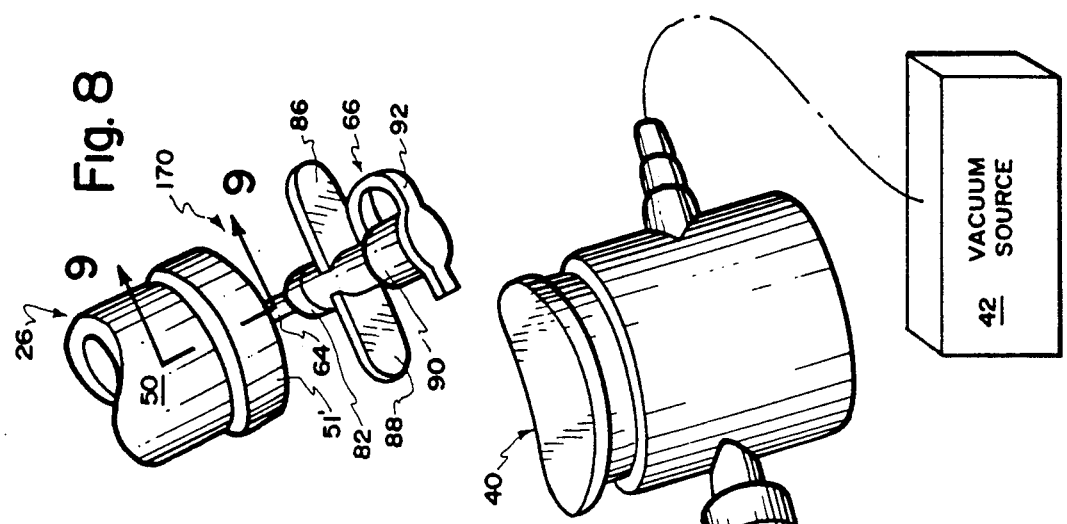
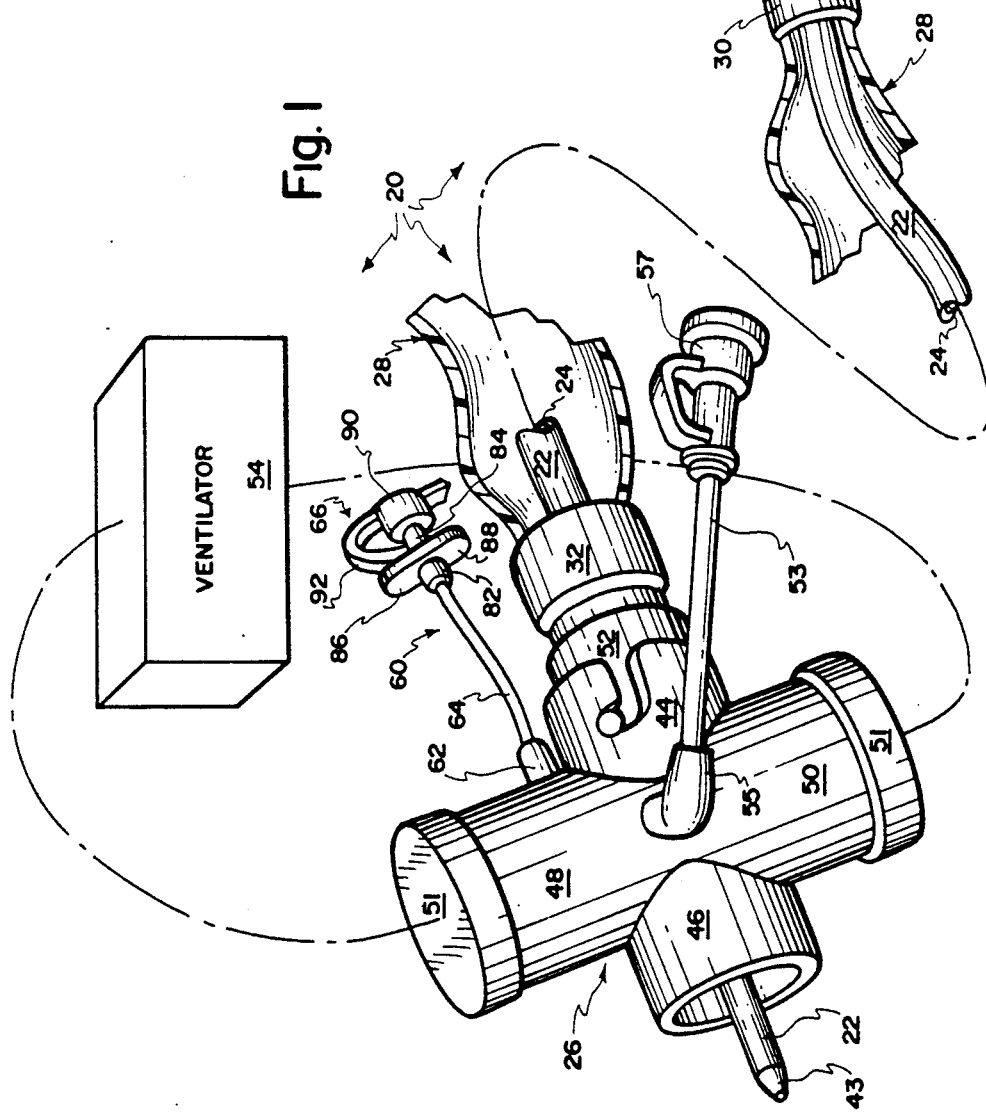

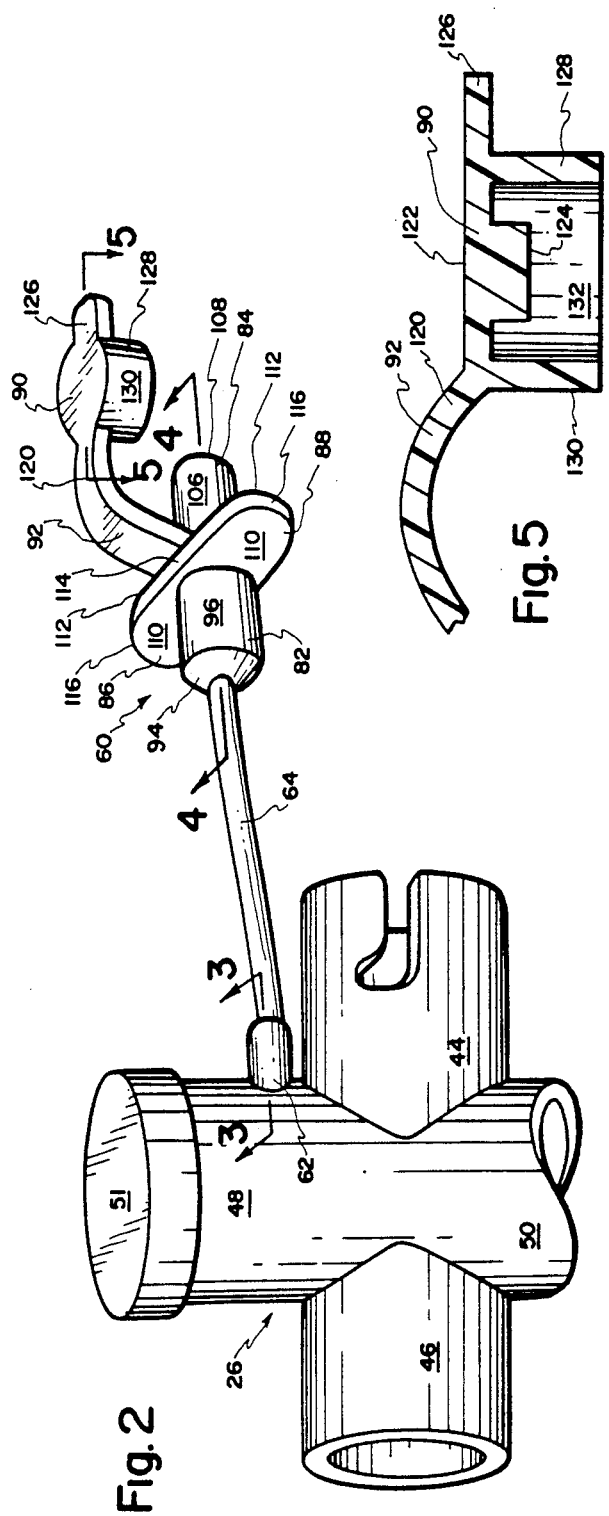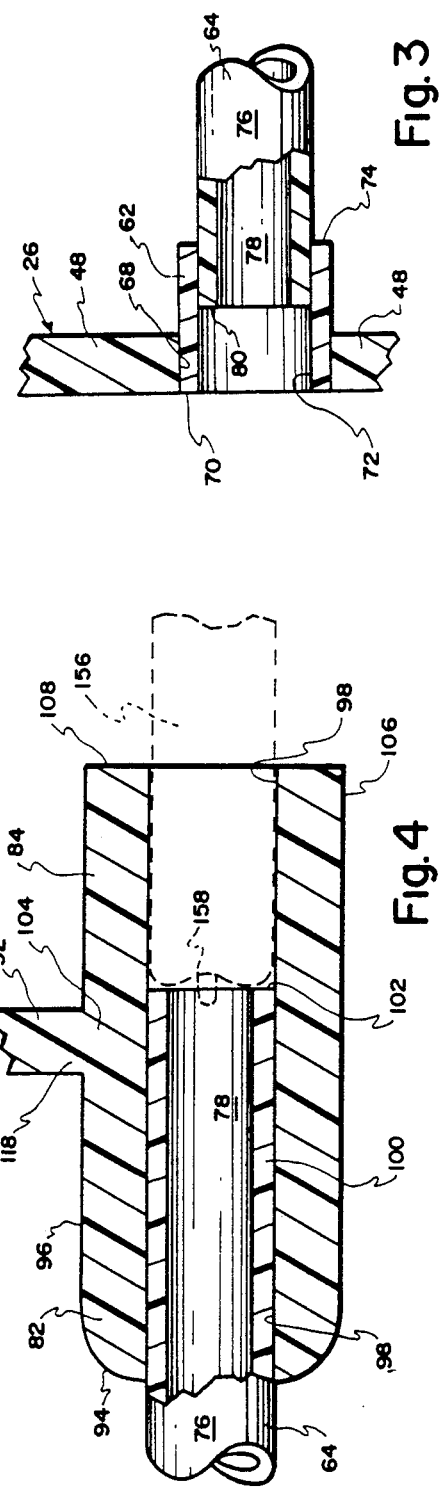

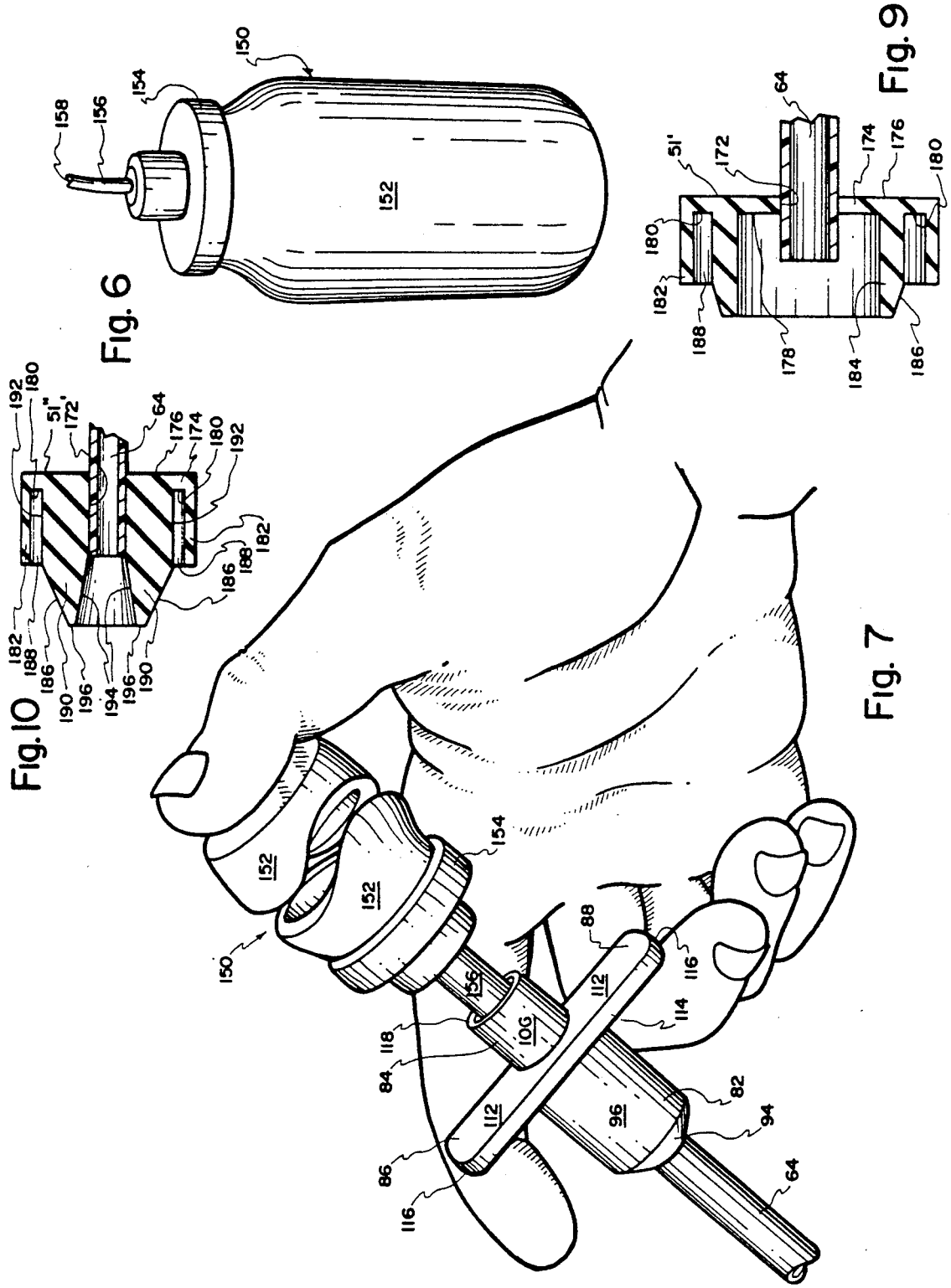

MEDICAL VENTILATING AND ASPIRATING APPARATUS AND METHODS

FIELD OF INVENTION

The present invention relates generally to ventilation and aspiration of the lungs of a medical patient and, more particularly, to a novel involuntary ventilating and aspirating apparatus, and related methods, by which a dose of medication may be selectively introduced into the lungs of a medical patient through a ventilating passage without disconnection of the apparatus or interruption of artificial ventilating under circumstances where aspiration can also occur without disconnection of the ventilating apparatus.

PRIOR ART

In the past, to Applicants' knowledge, simultaneous introduction of respiratory medication during aspiration or ventilation into the lungs of a patient on involuntary ventilating and aspirating apparatus has not been available.

Prior art techniques by which a metered dose of medication is introduced have been limited to use of a special adapter upstream in the ventilation circuit away from the patient or have been limited to non-aspirating applications. Such adapters are available from Instrumentation Industries, Inc. of Bethel Park, Pa., Marquest of Englewood, Colorado, and Monaghan Medical Corporation of Plattsburgh, N.Y.

BRIEF SUMMARY AND OBJECTS OF THE PRESENT INVENTION

In brief summary, the present invention is intended to overcome or substantially alleviate the aforementioned limitations of the prior art and comprises a novel ventilating/aspirating apparatus, and related methods, the apparatus comprising novel structure by which a metered predetermined dosage of medication is selectively, facilely and accurately introduced as an atomized spray into the respirating system of the patient during artificial ventilation, during aspiration and/or when ventilation is not occurring.

Accordingly, it is a primary object of the present invention to provide a novel ventilating and aspirating apparatus, and related methods which accommodate improved delivery of medication.

An important object of this invention is the provision of an aspirating/ventilating apparatus comprising novel structure for facile and accurate introduction of medication into the lungs of an intubated medical patient at any desired time without disconnection of the apparatus while preserving the aspirating capability of the apparatus.

A further significant object of the present invention is the provision of an aspirating/ventilating apparatus comprising novel structure and methods by which a metered predetermined dosage is introduced into an intubated patient during the inhalation part of ventilation when neither ventilation nor aspiration is occurring.

A further paramount object of the present invention is the provision of an aspirating/ventilating apparatus comprising structure and methods by which a controlled amount of medication is facilely, accurately and selectively introduced as an atomized spray into the respiratory system of a medical patient during artificial ventilation when neither ventilation nor aspiration is occurring.

A further valuable object of the present invention is the provision of an aspirating/ventilating apparatus comprising novel medication introduction structure and method steps by which medication is selectively introduced into the lungs of a patient without equipment disconnection or interruption in the ventilation cycle.

These and other objects and features of the present invention will be apparent from the detailed description taken with reference to the accompanying drawings.

BRIEF DESCRIPTION OF THE DRAWINGS

FIG. 1 is a perspective of a presently preferred embodiment of the present invention;

FIG. 2 is an enlarged fragmentary perspective of the tracheostomy fitting of the apparatus of FIG. 1 with the catheter, couplings, flexible envelope and irrigation tube removed for clarity;

FIG. 3 is a cross-section taken along lines 3—3 of FIG. 2;

FIG. 4 is a cross-section taken along lines 4—4 of FIG. 2;

FIG. 5 is a cross-section taken along lines 5—5 of FIG. 2;

FIG. 6 is a perspective representation of a pressurized canister containing respiratory medication;

FIG. 7 is an enlarged fragmentary perspective of the manner in which respiratory medication is introduced from a pressurized canister through an influent port in a tracheostomy fitting into an influent stream of involuntary ventilating gas prior to lung entry;

FIG. 8 is a fragmentary perspective of a second presently preferred embodiment of the present invention;

FIG. 9 is a fragmentary enlarged cross-section taken along line 9—9 of FIG. 8; and FIG. 10 is a cross-sectional view similar to that of FIG. 9 showing a further embodiment of the present invention.

DETAILED DESCRIPTION OF THE ILLUSTRATED EMBODIMENT

The aspirating/ventilating apparatus disclosed in U.S. Pat. No. 4,569,344 is a device, which among other things, is used to aspirate the lungs of a patient while receiving artificial or involuntarily ventilation. This device is attached to the patient's endotracheal tube by a tracheostomy fitting and is included as part of an overall ventilation circuit. The suction or aspirating catheter is enclosed within a plastic bag. As the patient requires artificial removal of secretions, the suction catheter is advanced through the fitting of the ventilating device into the patient's lung/airway system. Suction is thereafter applied to remove the secretions. Each lung/airway system may likewise be aspirated. The catheter is subsequently withdrawn into the plastic bag. Secretions are thus drawn into the lumen of the catheter tube and removed.

The present invention is directed toward structure by which a known metered amount of medication may be selectively, facilely and accurately introduced into the lungs of a medical patient during the artificial ventilation cycle or when neither ventilation or aspiration is occurring.

Reference is now made to the drawings wherein like numerals are used to designate like parts throughout. A presently preferred integrated ventilator/aspirating mechanism, generally designated 20, is illustrated in the drawings and embodies the principles of the present invention. The ventilating/aspirating apparatus 20 is exemplary of the present invention.

Ventilating/aspirating mechanism 20 is illustrated in FIG. 1 as being adapted for connection to a medical patient at a tracheostomy connector 26 or to an endotracheal tube which is left indwelling for repeated use over a protracted interval of time. Mechanism 20 comprises a central portion comprising a sterile internal aspirating catheter tube 22 having a hollow interior passageway 24 of sufficient capacity to aspirate secretions from the trachea and bronchus. The aspirating catheter tube 22 is formed of a suitable synthetic resinous material which is yieldable but shape-retaining when in an unstressed condition, such as medical grade transparent or translucent polyvinyl chloride and further comprises an annular wall essentially of uniform thickness throughout having typically small uniform inside and outside diameters. The outside diameter is selected to comfortably pass through the tracheostomy fitting 26 and into either lung/airway system of the patient.

The aspirating catheter tube 22 has sufficient strength to prevent buckling, bending and twisting of the catheter tube, which would otherwise occlude or tend to occlude the interior passageway of the catheter tube. In the assembled condition, the tube 22 is surrounded by a sack or flexible envelope 28, formed of suitable impervious synthetic resinous film material of medical grade, such as polyethylene film in sleeve form.

The flexible envelope 28 is compressible from end to end. This allows for ready manual manipulation of the catheter tube 22 by gripping action on the part of the user applied to the exterior of the envelope 28. The catheter tube 22 is controlled solely by manual manipulation thereof through the envelope.

The flexible envelope 28 is held by an interference fit at the opposite ends thereof by collars 30 and 32, respectively. The interference fit couplings 30 and 32 together with an aspirating vacuum controlled valve 40 and the tracheostomy tube connector 26 are illustrated as being of known components. These components are described in substantial detail in U.S. Pat. No. 4,569,344, the contents of which are incorporated herein by reference for purposes of simplifying this detailed description. It should be noted, however, that the interior of the catheter tube 22 is in fluid communication with the valve 40, which in turn is selectively caused to be in fluid communication with a vacuum source 42, such as a conventional hospital suction system. In short, when the catheter tube 22 is in the appropriate indwelling position in the lung/airway system of a medical patient, the valve 40 is manually actuated so that the vacuum of source 42 is applied to the hollow interior 24 of the catheter tube 22 thereby causing undesired secretions from the lung to enter the catheter tube through the tip opening 43 and to be removed via the hollow interior 24 of the catheter tube 22.

The tracheostomy tube connector 26 is illustrated as being in the form of a cross fitting. The fitting 26 provides an external seal against a loss of air or liquid pressures applied to the lung/airway system of a patient but accommodates snug slidable displacement of the catheter tube 22 through the fitting 26. The fitting 26 comprises first, second, third and fourth port structure 44, 46, 48 and 50. Ports 48 and 50 are illustrated as being closed by removable caps 51. Port structure 44 releasably connects through a fitting 52 to the distal end of the plastic envelope 28. Port structure 46 is appropriately fitted upon an exposed end of an endotracheal tube leading to the lung/airway system of the patient, while port structure 48 and 50, respectively, with the caps 51 removed, connect to the intake and exhaust terminals of a conventional ventilator 54. Thus, the ventilator 54 drives air through either port 48 or 50, respectively, with the caps 51 removed, connected to the output and exhaust terminals of a conventional ventilator 54. One port 48 or 50 may be used to accommodate both influent and effluent ventilations, with the other port 48 or 50 being left capped. Thus, the ventilator 54 drives air through either port 48 or 50 into the lung/airway system of the patient via port 46 under positive pressure and evacuates gases from the respiratory system of the patient via port 46 through the same or the other port 50 or 48.

Connector 26 also comprises a hollow irrigation tube 53 joined to the housing of connector 26 at hollow fitting 55. During periods of non-use, irrigation tube 53 is closed, at its distal end by a removable tethered plug 57. The irrigation tube is used to deliver an irrigation solution to the exterior of the catheter tube 22 to remove secretions therefrom during withdrawal of the catheter tube from the lung/airway system of a patient and to remove secretions from within the catheter tube after complete withdrawal. The specific structure and exact function of the irrigation tube and related parts are set forth in U.S. Pat. No. 4,569,344, to which reference may be made.

The tracheostomy fitting 26 comprises medication influent structure 60. Influent structure 60 comprises seriatum a proximal boss 62 integral with the wall of the fitting 26, a hollow central tube 64 and a distal hollow fitting 66. Together boss 62, tube 64 and fitting 66 comprise structure which defines a hollow medication passageway. The passageway is sufficiently small so that it does not materially effect either the ventilating cycle or the pressures required for the ventilating cycle when open.

As best seen in FIG. 3, the proximal boss 62 is illustrated as extending snugly through an aperture 68 in the wall 48 so as to be flush at its interior edge 70 with the interior surface of the wall 48. Preferably, a suitable adhesive or bonding agent immovably holds boss 62 in the aperture 68 as shown in FIG. 2. Boss 62 comprises a hollow interior surface 72 of predetermined uniform diameter and terminates in exposed blunt edge 74. Boss 62 is preferably formed of medical grade rigid shape retaining plastic, such as polyethylene.

The tube 64 may be of any desired length to accommodate introduction of a controlled dose of medication without encumbering the apparatus or altering the effectiveness of medication delivery. Preferably, tube 64 comprises a yieldable medical grade polyvinyl or other suitable synthetic resinous material. Tube 64 is illustrated as being of uniform inside and outside diameters at surfaces 76 and 78 thereby creating a uniform hollow bore and wall thickness. The outside diameter defined by wall 76 is substantially the same as the inside diameter at 72 of the boss 62. The proximal end 80 is snugly inserted into the interior of the boss 62 and secured as by suitable bonding or adhesive techniques. See FIG. 3.

Fitting 60 is of one-piece molded synthetic resinous material, such as polyvinyl. Fitting 60 comprises a proximally extending barrel 82, a distally extending barrel 84, opposed finger gripping flanges 86 and 88 and a cap 90 tethered at 92 to the barrel 84. See FIG. 2. As best seen in FIG. 4, the barrel 82 comprises a rounded exposed end surface 94. Surface 94 merges with exterior surface 96 which is of uniform diameter. The body of barrel 82 defines a central bore 98 the diameter of which is substantially the same as the outside diameter of tube 64 defined by surface 76. Thus, the distal end 100 of the tube 64 is snugly inserted into the bore 98 to the position illustrated in FIG. 4 and then glued, bonded or otherwise secured. Consequently, blunt distal edge 102 of the tube 64 is somewhat centrally disposed within the bore 98, which also extends through barrel 84.

Barrel 84 is integral at site 104, adjacent flanges 86 and 88, with barrel 82 and comprises an exterior exposed cylindrical surface 106 of a diameter illustrated as being the same as the diameter of the surface 96. Barrel 84 terminates in a blunt distal edge 108.

The flanges 86 and 88 are shown in FIG. 2 as being essentially elongated, planar and oppositely aligned. Each flange 86 and 88 comprises a first surface 110, a second surface 112, a uniform thickness defined by edge 114 which comprises rounded end 116. The flanges need to be substantially non-yieldable to stably withstand the force applied thereto by a medical attendant as hereinafter explained.

The tether 92 is shown as being of flat rectangular configuration, the proximal end 118 of which is integral with the barrel 84. See FIGS. 2 and 4. The distal end 120 of the tether is integral with the cap 90 at the top thereof. See FIGS. 2 and 5.

Cap 90, as best seen in FIG. 5, comprises a top flat wall 122 which is centrally cylindrically enlarged at projection 124. The top flat wall terminates in a radially-extending cantilevered tab 126, used to manually remove the cap from the barrel 84.

Top wall 122 integrally merges with cylindrical wall 128 which is shown as being of uniform thickness and comprises outside surface 130 and inside surface 132. The diameter of inside surface 132 is selected to be substantially the same as the outside diameter of barrel 84 at surface 106 and the diameter of projection 124 is selected to be substantially the same as the inside diameter of barrel 84 at bore surface 98 so that the cap 90 may be snugly manually force-fit and retained upon and within the distal end of the barrel 84 against inadvertent removal, as shown in FIG. 1.

Manual force applied to the tab 126 in a direction away from the barrel 84 will remove the cap 90 from the distal end of the barrel 84 as shown in FIG. 2.

It is conventional for respiratory medications in liquid form to be placed in a pressurized canister or container which comprises a top lid having a valve actuating exposed stem. One such conventional canister is shown in FIG. 6 and is generally designated as 150. Canister 150 comprises a glass or aluminum vial 152 closed by a valve-containing lid 154. The concealed valve is normally closed but is opened by depression of a spring biased hollow stem 156. As a consequence, the liquid medication, which is under gas pressure within the canister is discharged as an atomized spray through the hollow of the stem and out an effluent orifice 158 in the stem.

One example of the type of medication contained in a pressurized canister of the type described above is a 15 ml vial of Medihaler-Iso (isoproterenol sulfate) available from Riker Laboratories, Inc. of St. Paul, Minnesota.

The present invention is not limited to, but may utilize a canister such as canister 150.

It is readily apparent from an inspection of FIGS. 1 and 2 that during times of nonuse, the medication influent structure 60 is simply closed by force-fitting of the cap 90 over the end 108 of the barrel 84. This position is best illustrated in FIG. 1.

On those occasions when it is appropriate and timely to introduce a specific medication into the lungs/airway system of the patient, such is facilely achieved by use of the present invention. Medication may be introduced directly into the lung/airway system of a patient. Without interruption of an on-going ventilation cycle or when neither ventilation or aspiration is occurring.

More specifically, the user (doctor, nurse or technician) inserts the stem 156 of the canister 150 (FIG. 6) into the trailing end of the bore 98 at barrel 84 of the medication influent structure 60, after the cap 90 has been removed from the barrel 84, as shown in FIG. 2. The diameter of the bore 98 is selected so that the canister stem 56 has an outside diameter slightly less than the bore 98 but greater than the inside diameter of the tube 64 at central passageway 78. Thus, upon insertion, the stem 56 achieves the position illustrated in FIG. 4. The trailing edge 102 of the tube 64 functions as a stop preventing further insertion of the stem 156. At this time, by exerting further force upon the bottom of the canister as shown in FIG. 7, the stem 156 is displaced into the cap 154 counter to the bias applied against the stem 156. This opens the normally closed valve contained within cap 154 which dispenses a predetermined precise quantity of the medication desired from the canister as a spray through the stem, out the orifice 158 of the stem, down the tube 64, through the central passageway 78 and into the tracheostomy fitting 26. From thence, the atomized medication is dissipated and carried into the lung/airway system of the patient.

In reference to FIG. 7, it is to be appreciated that the presently preferred mode by which the valve of the canister cap 154 is opened occurs by placing the stem 156 into the hollow of the barrel 84 and thereafter placing the index and middle fingers around the opposed flanges 86 and 88, respectively, while applying thumb pressure to the bottom of the canister. Thus, the introduction of an exact dose of medication is achieved using one hand. It should also be understood that a canister of the type shown in FIG. 6 comprises a valve automatically closed after being opened following dispensing of a predetermined amount of medication. Of course, if two doses of the medication are desired, the canister is merely manually cycled twice, in the manner illustrated in FIG. 7, so that the desired amount of the atomized medication is discharged as explained above into the respiratory system of the patient.

Reference is now made to additional presently preferred embodiments of the present invention generally designated 170 and illustrated in FIGS. 8 through 10. Specifically, the embodiments of FIGS. 8 through 10 calls for the placement of the previously described medication influent structure 60 not in the wall of the fitting 26 at port 48 but centrally through one of the end caps of the fitting 26. This presumes that the opposite transversely disposed end cap 51 is removed and functions as the influent and effluent port for ventilating and exhaust gases from the patient. With reference to FIG. 8, the cap 51' force-fit upon the end of the port 50 is identical to the previously described cap 51, except a hole 172 (FIG. 9) has been centrally formed in cap 51. The cap 51' comprises a base wall 174 of substantially uniform thickness which comprises an exterior surface 176, and internal central interior surface 178 and a second interior surface 180. An external longitudinally-directed flange 182 of annular configuration is integral with the base wall 174. A second axially directed flange 184 is concentrically disposed within the flange 182, is annular and formed integrally with the wall 174. Annular flange or wall 184 is axially longer than flange 180 and comprises a beveled surface 186. Otherwise, annular wall 184 is somewhat transversely thicker than annular wall 182 and, apart from the bevel 186, each annular wall 182 and 184 is of uniform thickness. As can be seen from an inspection of FIG. 9, a uniform space 188 is thus defined between the annular walls 182 and 184.

The space 188 is slightly less than the thickness of the barrel 50 and the outside diameter of the wall 184 is slightly greater than the inside diameter of the barrel 50. Accordingly, as the cap 51' is advanced against the open end of the barrel 50, the distal edge of the barrel 50 will first contiguously engage the beveled surface 186 deflecting the wall 184 compressively toward the axis of the cap 51'. Ultimately, the edge of the barrel 50 becomes contiguous with the surface 180 and the adjacent portion of the barrel 50 is force-fit into space 188 and is compressively releasibly there retained.

With continued reference to FIG. 9, the tube 64 of the medication influent structure 60 is caused to be force-fit through the central aperture 172 so as to extend a short distance inwardly into the space existing within the annular wall 184. If desired, a suitable bonding agent or adhesive may be applied to secure the tube 60 in its inserted position through the aperture 172.

With specific reference to FIG. 10, it should be noted that identical numerals are used to designate those portions of FIG. 10 which are the same as shown and described in respect to FIG. 9. Only the differences will now be described. Specifically, in lieu of annular flange 184, the embodiment of FIG. 10 comprises a wedge-shaped body of material which expands transversely between tube-receiving aperture 172' and the annular space 188. This wedge-shaped body is designated as 190 in FIG. 10 and is integral with the base wall 174. A suitable bonding agent or adhesive may be applied to the surface of central bore 172' at the time the proximal end of the tube 60 is inserted so that the two are integrally joined. Note that the entire length of the proximal end of the tube 64 disposed within the cap 51" is contiguously supported by the wedge-shaped body 190. The wedge-shaped body 190 comprises an annular longitudinally directed surface 192, which defines one side of space 188. Body 190 also comprises outside beveled surface 186, inside beveled surface 194 and blunt proximal, transversely disposed edge 196, which bridges between beveled surfaces 186 and 194.

The bulk of the wedge-shaped body 190 stabilizes cap 51", with the beveled or conical surface 194 accommodating an immediate diffusion of medication entering the port 50 from the tube 64. The insertion of the cap 51" is essentially identical to the insertion of cap 51'.

Since the remainder of the medication influent structure illustrated in FIGS. 8 through 10 is identical to that illustrated and described in FIGS. 1 through 7, no further description of the components of the medication influent structure 60 is needed. Also, the operation of the embodiments of FIGS. 8-10 is substantially identical to the operation of the previously described embodiment of FIGS. 1 through 7 and, therefore, no further operational description is needed.

The invention may be embodied in other specific forms without departing from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by U.S. Letters Patent is:

1. A method of placing respiratory medication into the lung/airway system of a medical patient comprising the steps of:
    interposing ventilating/aspirating apparatus between the lung/airway system of a patient and a ventilator;
    causing the ventilator and the ventilating apparatus to involuntarily cycle influent ventilating gas to the lungs of the patient and to remove effluent gas from the patient through a tracheal tube;
    selectively introducing an aspirating catheter into the respiratory system to remove secretions from the lungs of the patient without disconnection of the ventilating apparatus;
    selectively introducing at any time a selected quantity of respiratory medication across a selectively actuated one-way valve and along a central passage of a pressurized hand-held container into the ventilating apparatus through a centrally unobstructed passageway of a fitting in which the valve of the container is actuated immediately adjacent the tracheal tube of a patient without disconnection of the ventilating apparatus or interruption of either the aforesaid ventilating or aspirating steps.

2. A method according to claim 1 wherein the selective introducing step comprises introducing the medication as an atomized spray through the centrally unobstructed passageway of said fitting.

3. A method according to claim 1 wherein the selective introducing of respiratory medication step comprises introducing the medication through selectively openable medication port structure in said fitting.

4. A method according to claim 1 wherein the introducing of medication step is preceded by the step of externally opening a normally closed end of the centrally unobstructed passageway and is followed by closing of the normally closed end.

5. A method of introducing medication into the lungs of a medical patient comprising the steps of:
    subjecting the patient to cycles of involuntary influent and effluent gaseous respiration;
    subjecting the patient to cycles of involuntary aspiration of secretions from the lungs without incapacitating said respiration capability;
    introducing medication in spray form from a pressurized container comprising a manually activated self contained, normally closed valve during said respiration cycle or between the respiration and aspirating cycles.

6. A ventilating/aspirating apparatus comprising:
    a hollow ventilating circuit comprising an at-patient hollow ventilating and aspirating fitting adapted to be interposed between a respirator and the lung-/airway system of a patient;
    an aspirating catheter tube reciprocably displaceable through said at-patient fitting;
    said fitting comprising medication influent structure;

the medication influent structure comprising closure means which can selectively be manually opened and closed and influent passageway means and orifice means, comprising means for receiving insertion and means for stopping further insertion of a stem of a pressurized-medication-containing container comprising a manually activated, self-contained, normally closed valve, where the influent passageway means merge with the hollow of the fitting.

7. A ventilating/aspirating apparatus according to claim 6 wherein the closure means comprises a cap selectively press-fit upon one end of the passageway means.

8. A ventilating/aspirating apparatus according to claim 7 wherein the cap is tethered to another portion of the medication influent structure.

9. A ventilation/aspirating apparatus according to claim 6 wherein the stopping means comprise an internal axial diameter less than the stem of the pressurized-medication-containing container but greater than a stem-contained dispensing orifice of the pressurized-medication-containing container and, by which, passageway means accommodate reciprocation of valve-opening means of a separate pressurized container of medication whereby a controlled dose of medication is discharged from the container into the passageway means.

10. A ventilating/aspirating apparatus according to claim 6 wherein the medication influent structure comprises opposite laterally extending finger grasping means by which introduction of medication to the passageway means is accommodated using a single hand.

11. A ventilating/aspirating apparatus comprising:
a hollow ventilating circuit comprising an at-patient hollow ventilating and aspirating cross-fitting comprising at least two tracheostomy orifices adapted to be interposed between a respirator and the lung-/airway system of a patient;
an aspirating catheter tube reciprocably displaceable through said at-patient cross-fitting;
said cross-fitting comprising medication influent structure;
the medication influent structure comprising closure means which can selectively be manually opened and closed and influent passageway means and orifice means, comprising means for receiving insertion and means for stopping further insertion of a stem of a pressurized-medication-containing container comprising a manually activated, self-contained, normally closed valve, where the influent passageway means merge with the hollow of the fitting.

12. A ventilating/aspirating apparatus according to claim 11 wherein the medication influent structure and one of the tracheostomy orifices, when unused in the respiratory circuit, comprise the same means.

* * * * *